United States Patent [19]

Amezcua

[11] 4,221,217

[45] Sep. 9, 1980

[54] NASAL DEVICE

[76] Inventor: Saul O. Amezcua, Mazatlan #118, Condesa Colony, Mexico City, Mexico

[21] Appl. No.: 901,464

[22] Filed: May 1, 1978

Related U.S. Application Data

[63] Continuation-in-part of Ser. No. 757,193, Jan. 6, 1977, abandoned.

[51] Int. Cl.[3] .................... A61M 15/08; A62B 23/06

[52] U.S. Cl. .................... 128/206.11; 128/203.22

[58] Field of Search .............. 128/140 N, 140 R, 198, 128/206, 203.22, 206.11

[56] References Cited

U.S. PATENT DOCUMENTS

| | | | |
|---|---|---|---|
| 855,573 | 6/1907 | Heath | 128/140 N |
| 878,223 | 2/1908 | Meisselbach | 128/198 |
| 1,311,461 | 7/1919 | Reynard | 128/198 |
| 1,322,375 | 11/1919 | Un | 128/140 N |
| 2,097,846 | 11/1937 | Strauch | 128/140 N |
| 2,715,904 | 8/1955 | Hill | 128/140 N |
| 2,751,906 | 6/1956 | Irvine | 128/140 N |
| 3,463,149 | 8/1969 | Albu | 128/206.11 X |
| 3,747,597 | 7/1973 | Olivera | 128/140 N |
| 4,030,491 | 6/1977 | Mattila | 128/140 N |

FOREIGN PATENT DOCUMENTS

| | | | |
|---|---|---|---|
| 477874 | 10/1969 | Switzerland | 128/140 N |

*Primary Examiner*—Henry J. Recla

*Attorney, Agent, or Firm*—Kendrick, Netter & Bennett

[57] ABSTRACT

An article for holding one or more replaceable elements in the nasal passages of a human being for affecting gases passing through such elements includes a loop-shaped clip having a holder for such elements, preferably at one or both ends of the loop.

7 Claims, 10 Drawing Figures

FIG. 1.
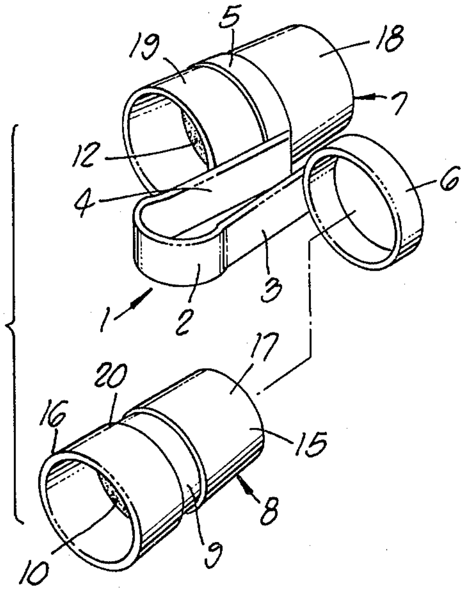
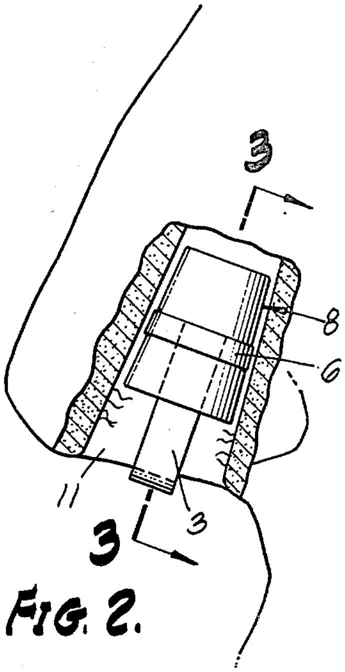
FIG. 2.
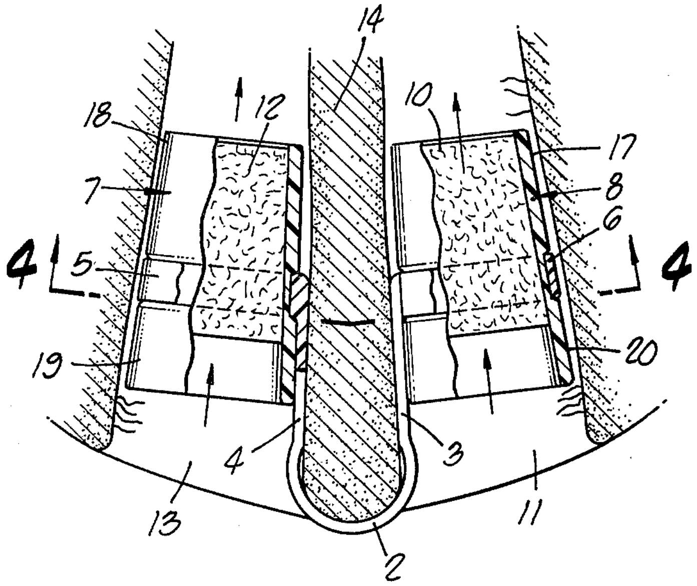
FIG. 3.
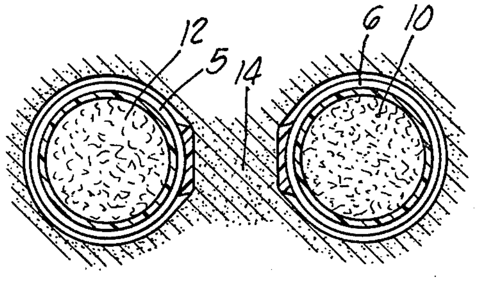
FIG. 4.

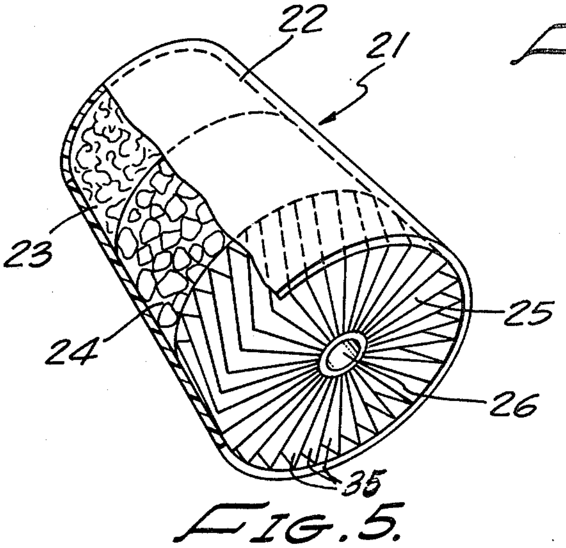
FIG. 5.
FIG. 6.
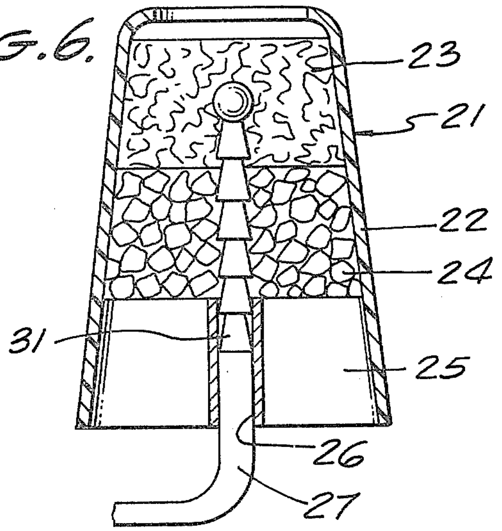
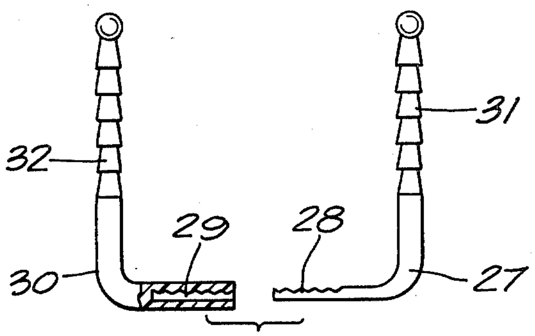
FIG. 7.
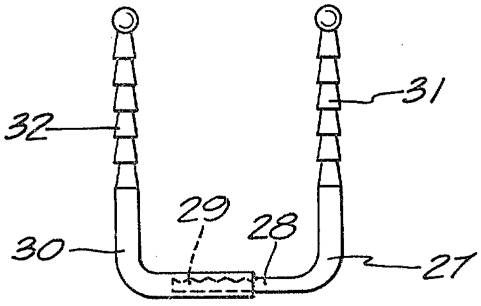
FIG. 8.
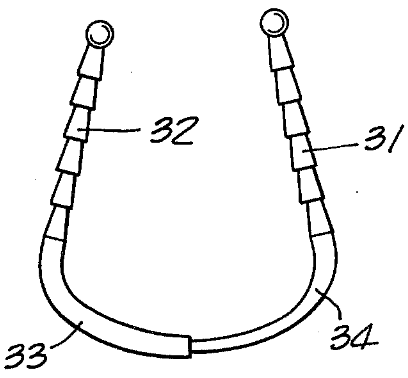
FIG. 9.
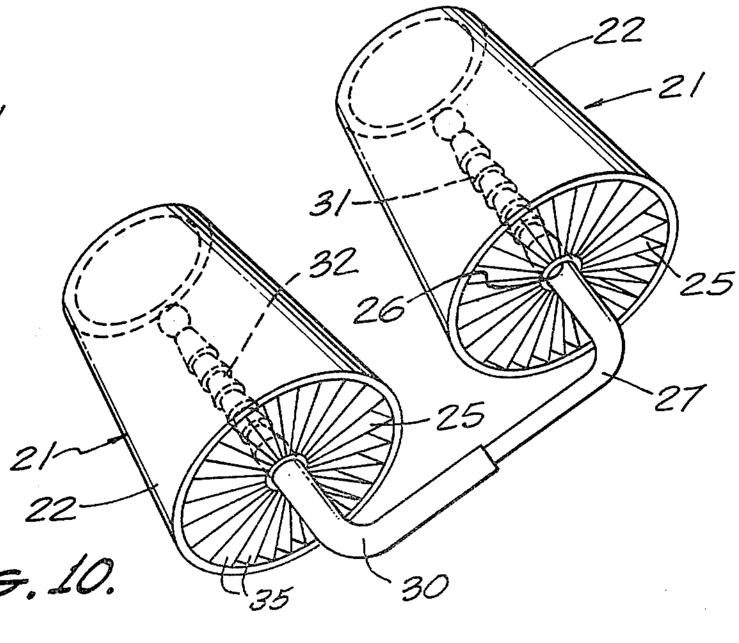
FIG. 10.

NASAL DEVICE

This application is a continuation-in-part of U.S. Ser. No. 757,193, filed Jan. 6, 1977, now abandoned and entitled NASAL DEVICE.

The invention relates to a device for holding gas-affecting means in one or both nasal passages of mammals, and especially the nasal passages of humans.

It is an object of this invention to provide a means for preventing passage of contaminants in the air through the nasal passages of mammals such as human beings with an article that holds one or more removable elements for filtering or otherwise decontaminating air passing through such elements.

Another object of the invention is to provide means for holding filters or other gas-affecting means in the nasal passages of mammals such as humans that do not inflame such nasal passages or cause discomfort to the user.

Another object of the invention is to provide means for holding one or more elements in one or both nasal passages of a human being or other mammal that are comfortable to wear, effectively filter or otherwise affect air passing therethrough, are appropriately shaped to prevent inhalation of such elements, and are readily removed and replaced with the same or with a different element.

Another object of the invention is to provide means for holding at least one removable filter or other air-affecting means in one or both nasal passages of mammals such as humans that may be expelled freely from nasal passages on sneezing or other violent discharge of fluids through the nasal passage, yet remain firmly, safely and comfortably in place during normal passage of fluids through the nasal passages.

To accomplish these and other objects, this invention provides a device comprising loop-shaped means for holding in at least one nasal passage of mammals such as human beings at least one removable means for affecting gases passing through such means.

The loop-shaped means is preferably U-shaped, and more preferably comprises a U-shaped device having a slightly flared or rounded portion at the closed end of the loop joined to a pair of flexible thin planar elements or arms. Although the inner surfaces of the arms or elements of the loop are preferably planar, they may also be rounded or otherwise shaped to facilitate the comfort of the wearer. These arms preferably converge from the junction with the rounded portion, where they are farthest apart, to the ends of the arms. The flared or rounded portion of the loop is at least slightly, and is preferably substantially less flexible than the converging elements joined thereto, and produces a pincer-like force upon the converging arms. This pincer-like force facilitates retention of the loop on the septum of a mammal by means of the force the converging arms or elements exert upon the septum after the new device is placed in the nose. In general, the elements or arms should exert sufficient force on the septum between the nasal passages of the mammal to ensure that the loop-shaped means will be retained within such nasal passages during the normal passage of air and other gases through such nasal passages.

In one embodiment, the loop-shaped means includes two engageable portions, each including arm means having thereon means for holding gas-affecting means. These engageable portions are preferably interfitting, with one portion terminating in a female section; the other, in a male section.

On at least one arm (preferably on both), and proximate at last one end, more preferably proximate both ends, of the loop-shaped means of the new device is at least one means for holding one or more removable gas-affecting means within a nasal passage. This means may be a wire loop, a clip, a saw-toothed portion, or preferably a hoop or open-ended cylinder. Where the loop-shaped means or saw-toothed portion is made of flexible plastic such as polyethylene or polypropylene, the loop may be made of the same or different plastic and may be integrally formed with the loop-shaped means. Alternatively, the hoop, the loop-shaped means, or both, may be made of a metal and particularly of a precious metal such as gold, platinum or silver. The external surface of the hoop should be sufficiently smooth and even to avoid substantial irritation or inflammation of nasal passages.

Whatever means is provided at one or both ends of the loop for holding the gas-affecting means, the device will include at least one such gas-affecting means proximate one or both ends of the loop. Preferably, the gas-affecting means is removably retained within a sleeve (preferably a frusto-conical sleeve) having a smooth external surface.

In one embodiment, on its external surface, this sleeve has means which are complementary with the means for holding the sleeve proximate an end of the loop. In the preferred embodiment, such means is a circumferential groove in the external surface of the sleeve that fits snugly within, but is removable from the holding means on one or both arms, preferably proximate one or both ends of the loop-shaped means. Alternatively, the sleeve may simply have an external surface shape that is retained by friction within the holding means proximate one or both ends of the loop.

In another embodiment, the frusto-conical sleeve may be fitted with filter means that includes means for removably engaging an arm of a loop-shaped means. For example, where the arm includes a saw-toothed portion, the filter means may include passage means for receiving and engaging the saw-toothed portion.

Whether or not a removable sleeve is provided for holding the gas-affecting means, the device of this invention must have at least one removable gas-affecting means on at least one arm of the device, preferably proximate at least one end of the loop-shaped means. Such gas-affecting means include means for filtering air passing through nasal passages, medicaments that are designed to mix with air or other gases passing through nasal passages, and so on. Preferably, the gas-affecting means is at least one filter that at least partially fills the sleeve or other means for holding the gas-affecting means proximate one or both ends of the loop-shaped means. More preferably, the filter means consists of coconut fiber charcoal microcells having dimensions that will permit the free inhalation and exhalation of air or oxygen, yet will be sufficiently dense to filter substantial quantities of solid pollutants from the air, oxygen or other gas passing through.

The drawings which accompany this application illustrate two preferred embodiments of the invention, and include:

FIG. 1, which is a perspective view of one embodiment of the new device with one means for holding gas-affecting means removed from the loop-shaped means, and with the other, snap-fitted into a hoop on the loop-shaped means;

FIG. 2, which shows a side view of the embodiment shown in FIG. 1 in place on the septum between the nasal passages of a human being;

FIG. 3, which is a cross-sectional front view of the embodiment shown in FIG. 1, taken along the plane indicated by arrows 3—3 in FIG. 2, and shows the new device in place on the septum between the nasal passages of a human being;

FIG. 4, which is a cross-sectional view taken along the planes indicated by arrows 4—4 of FIG. 3, and shows a bottom view of the new device in place on the septum between the nasal passages of a human being;

FIG. 5 is a perspective view of one embodiment of the filter means for use with a second embodiment of the device of this invention;

FIG. 6 is a cross-sectional view of the filter means shown in FIG. 5 with an arm of the loop-shaped means received and engaged within passage means in the filter means;

FIGS. 7 and 8 show a second embodiment of the loop-shaped means of the device of this invention including two engageable, interfitting portions having saw-toothed arms for engaging the filter means;

FIG. 9 shows a modification of the embodiment of the loop-shaped means shown in FIG. 8 where the arms of the loop-shaped means converge toward one another; and FIG. 10 shows the second embodiment of the new device of the invention including the loop-shaped means of FIG. 8 and the filter means of FIG. 5.

Referring now in more detail to FIGS. 1 through 4 of the drawings, the new device, generally designated 1, comprises a loop-shaped means having a slightly rounded or flared bulb-shaped base 2 and a pair of integrally formed, convergent arms or elements 3 and 4. Proximate the ends of arms 3 and 4 are integrally-formed hoops 5 and 6. Removably fitted within hoop 5 is frusto-conical sleeve 7, which is at least partially filled with gas-affecting means 12, here, a filter for removing solid particles from air. Detached from hoop 6 is frusto-conical sleeve 8 having therein a circumferential groove 9 whose depth and width are complementary with the dimensions of hoop 6. As FIG. 1 shows, hoop 6 is a cylinder open at both ends, as is hoop 5. Sleeve 8 has a frusto-conical shape, which means that end portion 15 has a smaller circumference than end portion 16. Sleeve 8 is fitted within hoop 6 by passing end portion 15 of sleeve 8 into the interior of hoop 6 and sliding the sleeve forward until circumferential groove 9 seats itself within the interior of hoop 6. Removal of sleeve 8 from hoop 6 facilitates removal of gas-affecting element 10 from the sleeve and replacement of that element with another of the same or of a different kind. It is not essential that sleeve 8 be removable from hoop 6 or that sleeve 7 be removable from hoop 5, but this construction facilitates removal and replacement of the gas-affecting elements in each sleeve.

The arms or elements 3 and 4 of the loop-shaped device 1 are convergent, and are spaced sufficiently closely to ensure that the loop will exert enough force on the walls of the septum 14 between the nasal passages 11 and 13 to retain the loop-shaped means within the nasal passages during normal flow of gases therethrough. Thus, as best seen in FIG. 3, elements 3 and 4 press against septum 14 between nasal passages 11 and 13, ensuring that all gases passing into these nasal passages in the direction indicated by the arrows will pass through removable filter elements 10 and 12 held within sleeves 7 and 8. Sleeves 7 and 8 each have two distinct regions. Sleeve 8 has region 17 which has an outer circumference that is slightly smaller than the circumference of the portion of the nasal passage in which region 17 fits. Region 20 has an outer surface that fits closely against the outer wall of arm or element 3 which in turn fits snugly against septum 14, and also fits snugly against the walls of nasal passage 11. This ensures that air passing through filter means 10 fitted within sleeve 17 will not bypass the filter element, yet only a small portion of sleeve 8 rests directly against the nasal passage wall. Sleeve 7 has region 18 which corresponds to region 17 of sleeve 8, and region 19 which corresponds to region 20 of sleeve 8.

The embodiment of the device illustrated in FIGS. 1 through 4 of the drawings is made of plastic, and the loop-shaped means and the hoops 5 and 6 are integrally formed with the loop-shaped means. Though the hoops and loop are made of the same plastic in the device as shown, this is not essential. Each hoop may be made of a substance different from the loop. If desired, each hoop on a given loop may be made of a different substance than the other hoop on that loop. Sleeves 7 and 8 are made of plastic, typically polyethylene, and each of these sleeves is fitted with a filter element which may be made of coconut fiber charcoal microcells. Alternatively, elements 10 and 12 may be made of slow-release medication which mingles with air passing through the elements, and into the lungs.

Referring now to FIGS. 5 through 10 of the drawings, FIG. 5 shows a second embodiment 21 of the filter means used in the device of this invention. Filter means 21 includes frusto-conical sleeve 22 having removably fitted therewithin fibrous filter means 23, adsorbent charcoal layer 24, and multi-passage packing means 25. At the top of sleeves 22, flanges 35 and 36 prevent the escape of the fibrous filtering material but permit inflow and outflow of air through the sleeves. The sleeves themselves are sufficiently flexible to permit expansion and contraction as air passes through the filter means. Packing means 25 prevents escape of the adsorbent charcoal material from sleeve 22, and provides some filtering action. Packing means 25 includes a plurality of flat, blade-like elements 35 and hub-like passage means 26 for receiving and engaging means on the arm of the loop-shaped means of the nasal device, as better illustrated in FIG. 6. As FIG. 6 shows, passage means 26 engages saw-toothed portion 31 on arm means 27 of the new device. Saw-toothed portion 31 may be withdrawn from passage means 26 for purposes of replacing one or more of the gas-affecting means within sleeve 22.

FIGS. 7 and 8 show an embodiment of the loop-shaped means comprising two engageable, interfitting portions 27 and 30. Portion 27 includes integrally-formed arm and saw-toothed filter engaging means 31. Similarly, portion 30 includes arm 32 which has integrally formed thereon saw-toothed filter engaging means. Portion 30 includes female means 29, which receives male means 28 of portion 27 to form the loop-shaped means of the device. FIG. 8 shows male means 28 fitted within female means 29 to form a complete loop-shaped means.

FIG. 9 illustrates a modification of this embodiment in which arms 33 and 34 converge toward one another. In this modification, with the filter means in place on the saw-toothed portions 31 and 32, the new device securely engages the septum between the nasal passages of a human being, insuring that the device is retained firmly within those passages.

FIG. 10 shows the complete embodiment of the new device including the filter means 21 shown in FIG. 5 and the loop-shaped means shown in FIGS. 7 and 8. Preferably, but not necessarily (See FIG. 10), the loop-shaped means includes convergent arms as shown in FIG. 9.

What is claimed is:

1. An article comprising at least one removable means for affecting gases passing therethrough, and loop-shaped means for holding in at least one nasal passage said at least one removable gas-affecting means, said loop-shaped means including means proximate at least one end of the loop for engaging and holding said gas-affecting means, said gas-affecting means including hollow sleeve means having an open first end diverging to an open second end, said first end having an inwardly directed flange, a removable gas-affecting element means in said sleeve means, said flange preventing the escape of said element means from said first end of said sleeve means, a multi-passage packing means mounted within said second end for preventing the escape of said element means from said second end, said packing means having a cylinder mounted therein in the axial direction of said sleeve means, said cylinder having an axially extending bore therethrough, said element means including passage means aligned with said bore of said cylinder, said means proximate at least one end of said loop for engaging and holding said gas-affecting means extending into said bore and said passage means and being removably secured therein whereby said element means and said packing means alone receive and engage the engaging means on said loop.

2. The article of claim 1 wherein said loop-shaped means comprises means proximate both ends of said loop for holding separate sleeve means for said removable gas-affecting element means.

3. The article of claim 2 wherein said loop-shaped means comprises two engageable portions, each including an arm means.

4. The article of claim 2 wherein said loop-shaped means comprises convergent arms having thereon the means for engaging said gas-affecting means.

5. The article of claim 2 wherein said sleeve means of said removable gas-affecting means is a frustoconical-shaped hollow sleeve having said gas-affecting element means within said sleeve.

6. The article of claim 5 wherein the means in the interior of said sleeve is a removable air-filtering means.

7. The article of claim 6 wherein the gas-affecting means includes adsorbent charcoal and means for retaining said adsorbent charcoal within said sleeve.

* * * * *